United States Patent [19]

Sandvig et al.

[11] Patent Number: 5,002,047
[45] Date of Patent: Mar. 26, 1991

[54] ORTHOTIC PADS AND METHODS

[75] Inventors: Timothy C. Sandvig, Woodville, Wis.; Dennis C. Bartizal, Woodbury, Minn.

[73] Assignee: Minnesota Mining and Manufacturing Company, St. Paul, Minn.

[21] Appl. No.: 93,408

[22] Filed: Sep. 4, 1987

Related U.S. Application Data

[63] Continuation-in-part of Ser. No. 903,281, Sep. 3, 1986, and Ser. No. 15,972, Feb. 18, 1987, Pat. No. 4,223,070, which is a continuation-in-part of Ser. No. 784,345, Oct. 4, 1985, Pat. No. 4,633,827.

[51] Int. Cl.$^5$ .............................................. A61F 5/04
[52] U.S. Cl. .................................... 128/90; 128/91 R
[58] Field of Search ............. 47/56, 64; 128/90, 91 R, 128/595, 614, 155, 156; 252/182

[56] References Cited

U.S. PATENT DOCUMENTS

| | | | |
|---|---|---|---|
| 1,914,049 | 6/1933 | Smith | 128/595 |
| 2,650,212 | 8/1953 | Windemuth | 260/75 |
| 2,759,475 | 8/1956 | Wan Swaay | 128/90 |
| 2,800,129 | 7/1957 | Van Swaay | 128/90 |
| 2,973,529 | 3/1961 | Silveman | 128/595 |
| 3,040,740 | 6/1962 | Parker | 128/90 |
| 3,048,169 | 8/1962 | Pierce | 128/90 |
| 3,301,252 | 1/1967 | Mahoney, Jr. | 128/90 |
| 3,320,347 | 5/1967 | Greenawalt | 128/595 |
| 3,373,741 | 3/1968 | Hill et al. | 128/90 |
| 3,375,822 | 4/1968 | Rose | 128/90 |
| 3,572,330 | 3/1971 | Gander | 128/90 |
| 3,608,238 | 9/1971 | Reuter | 47/64 |
| 3,656,475 | 4/1972 | Hanrahan | 128/90 |
| 3,728,206 | 12/1973 | Buese | 161/112 |
| 3,763,858 | 10/1973 | Buese | 128/156 |
| 3,799,755 | 3/1974 | Rack | 47/56 |
| 3,819,796 | 6/1974 | Webster et al. | 264/321 |
| 3,847,722 | 11/1974 | Kistner | 161/109 |
| 3,874,376 | 4/1975 | Dart et al. | 128/90 |
| 3,882,857 | 5/1975 | Woodall, Jr. | 128/90 |
| 3,889,417 | 6/1975 | Wood et al. | 47/56 |
| 3,900,024 | 8/1975 | Lauber et al. | 128/91 R |

(List continued on next page.)

FOREIGN PATENT DOCUMENTS 0223380  1/1987  European Pat. Off. .
54-100181  8/1979  Japan ............................. 94 A/237
83/01736  5/1983  PCT Int'l Appl. .

OTHER PUBLICATIONS

"The Modified Silicone Rubber Playing Cast", J. A. Bradley, *The Physician and Sportsmedicine*, vol. 10, No. 11, Nov. 1982.

"Soft Playing Splint for Protection of Significant Hand and Wrist Injuries in Sports", J. A. Bergfeld et al., from the 48*th Annual Meeting of the American Academy of Orthopaedic Surgeons*, Las Vegas, Nev., Feb. 1981.

"Cast Tips-Silicone (Sports) Cast Application", C. Henderson, *Online Communications*, a publication of the National Association of Orthopaedic Technologists, vol. 4, No. 6, Nov./Dec. 1986.

Electro Insulation Corporation product information and letter from same.

U.S. Ser. No. 06/903,281 (allowed)-"Curable Material for Semi—Rigid Resilient Orthopedic Support".

*Primary Examiner*—Robert A. Hafer
*Assistant Examiner*—Michael Brown
*Attorney, Agent, or Firm*—Gary L. Griswold; Walter N. Kirn; Philip M. Goldman

[57] ABSTRACT

The present invention relates to an orthotic blank that includes an open-celled foam sheet impregnated with a water curable, isocyanate functional, polyurethane prepolymer resin. The orthotic blank can be used according to the method of this invention to prepare an orthotic pad bearing the impression of a body part to be supported and/or cushioned. The resultant orthotic pad exhibits both proper weight-bearing strength and cushioning properties for effective and comfortable use.

22 Claims, 2 Drawing Sheets

U.S. PATENT DOCUMENTS

| | | | |
|---|---|---|---|
| 3,935,355 | 1/1976 | Kuhn | 128/90 |
| 3,985,128 | 10/1976 | Garwood et al. | 128/89 |
| 3,998,219 | 12/1976 | Mercer et al. | 128/90 |
| 4,019,506 | 4/1977 | Eschmann | 128/90 |
| 4,060,075 | 11/1977 | Blomer et al. | 128/90 |
| 4,083,127 | 4/1978 | Hanson | 36/93 |
| 4,134,397 | 1/1979 | Gianakakos et al. | 128/90 |
| 4,144,658 | 3/1979 | Swan, Jr. | 36/117 |
| 4,182,056 | 1/1980 | Dalebout | 36/117 |
| 4,193,395 | 3/1980 | Gruber | 128/90 |
| 4,211,019 | 7/1980 | McCafferty | 128/595 |
| 4,232,457 | 11/1980 | Mosher | 128/595 |
| 4,235,228 | 11/1980 | Gaylord, Jr. et al. | 128/91 |
| 4,245,410 | 1/1981 | Molitor | 36/117 |
| 4,255,202 | 3/1981 | Swan, Jr. | 106/122 |
| 4,280,489 | 7/1981 | Johnson, Jr. | 128/80 H |
| 4,301,564 | 11/1981 | Dalebout | 12/146 R |
| 4,309,990 | 1/1982 | Brooks et al. | 128/90 |
| 4,315,703 | 2/1982 | Gasper | 405/264 |
| 4,323,061 | 4/1982 | Usukura | 128/90 |
| 4,325,380 | 4/1982 | Malkin | 128/581 |
| 4,331,134 | 5/1982 | Brooks et al. | 128/90 |
| 4,346,525 | 8/1982 | Larsen et al. | 36/69 |
| 4,347,213 | 8/1982 | Rogers, Jr. | 264/510 |
| 4,370,976 | 2/1983 | Wanchik et al. | 128/77 |
| 4,376,438 | 3/1983 | Straube et al. | 128/90 |
| 4,411,262 | 10/1983 | Von Bonin et al. | 128/90 |
| 4,414,762 | 11/1983 | Salomon et al. | 36/117 |
| 4,419,261 | 12/1983 | Takahashi | 252/182 |
| 4,427,003 | 1/1984 | Fennimore et al. | 128/90 |
| 4,433,680 | 2/1984 | Yoon | 128/90 |
| 4,439,934 | 4/1984 | Brown | 128/614 |
| 4,442,833 | 4/1984 | Dahlen et al. | 128/90 |
| 4,450,833 | 5/1984 | Brooks et al. | 128/90 |
| 4,451,310 | 5/1984 | Lairloup | 156/78 |
| 4,470,782 | 9/1984 | Zimmerman, Jr. et al. | 425/2 |
| 4,502,479 | 3/1985 | Garwood et al. | 128/90 |
| 4,510,700 | 4/1985 | Brown | 36/44 |
| 4,519,856 | 5/1985 | Lazzara | 156/49 |
| 4,520,581 | 6/1985 | Irwin et al. | 36/88 |
| 4,522,777 | 6/1985 | Peterson | 264/223 |
| 4,565,250 | 1/1986 | Vasko | 168/12 |
| 4,597,196 | 7/1986 | Brown | 36/44 |
| 4,598,826 | 7/1986 | Shinbach | 206/620 |
| 4,609,578 | 9/1986 | Reed | 428/76 |
| 4,628,621 | 12/1986 | Brown | 36/44 |
| 4,638,795 | 1/1987 | Richter et al. | 128/90 |
| 4,667,661 | 5/1987 | Scholz et al. | 128/90 |
| 4,683,877 | 8/1987 | Ersfeld et al. | 428/317.3 |
| 4,705,840 | 11/1987 | Buckanin | 528/53 |
| 4,893,617 | 1/1990 | Bartizal et al. | 128/90 |
| 4,946,726 | 8/1990 | Sandvig et al. | 428/76 |

ORTHOTIC PADS AND METHODS

RELATED APPLICATIONS

This application is a continuation-in-part of the following U.S. applications: Ser. No. 903,281, filed Sept. 3, 1986 for "Curable Material for Semi-rigid Resilient Orthopedic Support", now pending; and Ser. No. 15,972, filed Feb. 18, 1987 for "Orthopedic Splinting Articles and Methods", now U.S. Pat. No. 4,223,070 (which is a continuation-in-part of Ser. No. 784,345, filed Oct. 4, 1985 for "Orthopedic Casting Article and Method", now U.S. Pat. No. 4,633,827); the disclosure of each of which is incorporated herein by reference.

TECHNICAL FIELD

The present invention relates to the field of orthotic pads, useful for supporting and/or cushioning various parts of the body. More particularly, this invention relates to materials suitable for use as such orthotic pads, and to methods of preparing orthotic pads using such materials.

BACKGROUND ART

Orthotic pads are generally materials that are used in apposition to a mammalian body part in order to support and/or cushion that body part. Such pads can be used alone, i.e., as orthotic articles themselves, or in conjunction with other orthotic devices, e.g., harnesses, braces, straps and the like. Generally either the pad, the device, or both are custom-fitted in order to directly address and resolve the user's orthopedic needs.

Such pads can be used in a variety of ways including, e.g., as cushioning, such as for sports equipment or for therapeutic orthotic devices; as a support for weight-bearing applications, such as within an artificial leg; as padding within an immobilizing device, such as a cast; for protection from physical impact with another object, and so on.

The types of materials typically used for such purposes are as widely diverse as the uses themselves. For instance, materials such as trapped air, air bladders, foam rubber, styrofoam and felt are frequently used, depending on the application. See, for example, U.S. Pat. Nos. 4,280,489, 4,347,213, 4,370,976 and 4,565,250. Such materials generally have either sufficient strength for weight-bearing applications or sufficient resilience for comfort, but not both. Nor do the materials generally permanently conform with much accuracy to the shape of the body unless specially prepared, e.g., cut, molded or sculpted in an indirect manner.

Other types of materials, such as two-part foams and injectable foams can often be conformed to the shape of the body, are frequently somewhat stronger, and have been used for such purposes as ski boot inserts. See, e.g., U.S. Pat. Nos., 4,083,127, 4,144,658, 4,182,056, 4,245,410, 20 4,255,202, 4,301,564, and 4,414,762. Their use however is generally restricted to applications in which an outer shell, e.g., a portion of the ski boot itself, is available to contain the foam after it is mixed or injected and as it sets and cures. Moreover, the resultant cured foam would generally exhibit uniform density throughout its structure, and, in turn, uniform weight-bearing strength and cushioning properties, regardless of the potentially differing needs of different portions of the opposing body part.

A particularly important area for the use of orthotic pads is in the field of footwear, i.e., as orthotic footpads. Such orthotic footpads are typically prepared and fitted by an orthopedist or podiatrist and used to correct or compensate for certain orthopedic problems and abnormalities, e.g., in the foot itself, or perhaps even in the gait or posture of the patient.

Orthotic footpads can be used as inserts within other footwear, e.g., inside shoes or boots, or can be used alone, e.g., as the soles of shoes, or as custom-made sandals or portions of sandals. Materials described as useful for orthotic footpads and other devices include those described, e.g., in U.S. Pat. Nos., 4,211,019, 4,232,457, 4,325,380, 4,346,525, 4,439,934, 4,470,782 4,510,700, 4,520,581, 4,522,777, 4,597,196 and 4,628,621.

In selecting suitable materials for the preparation of orthotic pads, several criteria must be considered. Firstly, the materials should be of a type that can be quickly, easily, safely and permanently formed to the desired shape and position. Further, the finished orthotic pad should be sufficiently strong for its intended (e.g., supportive) purpose, yet should be sufficiently soft and resilient to be comfortable in use, e.g., while supporting weight, cushioning, and so on. Lastly, the finished orthotic pad should be durable enough to withstand the rigors of repeated and demanding use. Materials heretofore described in the art as useful for preparing orthotic pads can meet only some of these qualities but not all.

From the foregoing, it will be appreciated that improved materials and methods are needed for preparing orthotic pads that are readily conformable, and have proper weight-bearing strength as well as cushioning properties.

SUMMARY OF THE INVENTION

The present invention relates to an article and method suitable for forming an orthotic pad which effectively fulfills the aforementioned needs. Additionally, the article of the present invention greatly simplifies the preparation of orthotic pads.

According to a presently preferred embodiment of the invention, an orthotic blank is provided which comprises a conformable, curable substrate. Preferably, the blank comprises an open-celled foam sheet impregnated with a water-curable, isocyanate functional, prepolymer resin. The orthotic pad is formed from the blank by activating the prepolymer resin, applying and conforming the blank to a part of the body, and holding the blank in place as it sets. When cured, the resultant orthotic pad bears an impression of the body part, i.e., it is closely and permanently conformed to the shape and position of the body part held in apposition to the orthotic blank during curing. The cured orthotic pad also exhibits both proper weight-bearing strength and cushioning properties, in order to support and/or cushion that body part.

The modulus of the cured orthotic pad, as defined below, can be determined and used as an indication of the ability of the pad to comfortably support weight, while the resilience, also defined below, can be determined as well, and used as an indication of the cushioning properties of the cured orthotic pad. Significantly, the resultant cured pad can exhibit "variable modulus and resilience", i.e., the modulus and resilience of portions of the resultant pad will vary according to the degree each portion was compressed as it cured. As a result, the ability of the cured pad to support and/or cushion the body part directly correlates with the needs of each portion of the opposing body part. The pad is most dense, and therefore has a higher modulus and is slightly more resilient, in areas where it was most compressed during curing. As a result, denser areas are better able to provide support, whereas less dense (lower modulus, slightly less resilient) areas are better able to provide a cushion effect.

Because the foam sheet itself, before impregnation with resin, is pliant and extensible, the conformability of the resin-impregnated foam sheet is quite good. Surprisingly, the foam sheet can be resin-loaded to a very high degree and thereby impart the modulus and resilience desired in the cured orthotic pad. Also surprisingly, after resin-loading the foam sheet to the extent necessary to achieve the desired properties, the resultant orthotic pad still exhibits variable modulus and resilience.

The foam sheets of the present invention can frequently be impregnated in a solvent-less manner, thereby avoiding any potential problem arising from prolonged contact of residual traces of solvent with the body part.

Good conformability, moldability and omnidirectional extensibility in applying the resin-impregnated foam sheet are made possible with the present invention. As a result, good alignment of the cured orthotic pad with respect to the body part can be achieved. Another benefit of the present invention is that the surface of the resin-impregnated foam sheet is less tacky than would be expected, thereby greatly facilitating application of the pad. Furthermore, by the addition of catalysts as described herein, the blanks of the present inventions are able to be set and cured within a short period of time, yet with a low exotherm, thereby providing both convenience and comfort for the subject.

These and other features of the present invention will become more fully apparent from the following description and appended claims, taken in conjunction with the accompanying Drawing.

DETAILED DESCRIPTION

Figure 1:
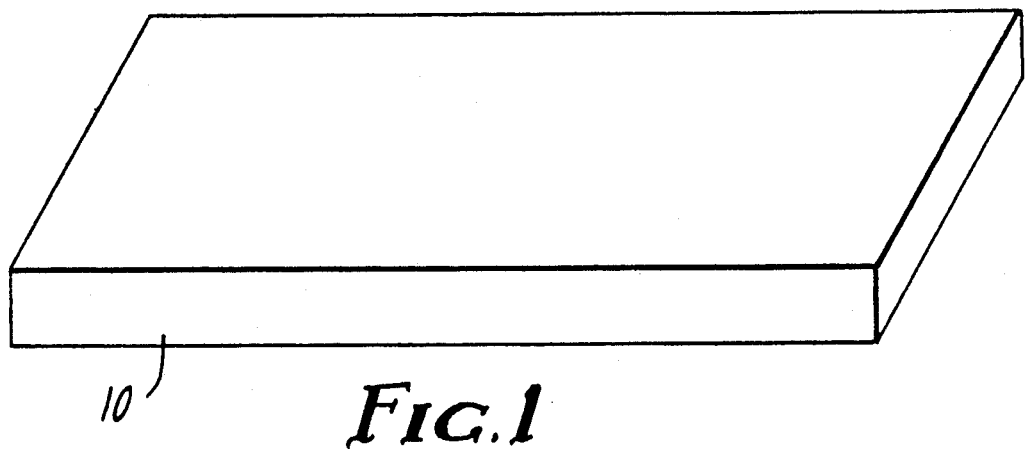
FIG. 1 is a perspective view of a preferred embodiment of a blank for an orthotic footpad of the present invention prior to application.

The subject matter of the present application is a continuation-in-part of the subject matter of the co-pending applications cited above.

Application Ser. No. 903,281 discloses a curable orthopedic support material that comprises a flexible sheet material, such as a knitted fabric, impregnated with a liquid resin system which cures upon exposure to a curing agent into a semi-rigid, resilient support device.

Application Ser. No. 15,972 discloses orthopedic splinting articles and methods, utilizing an open-celled foam sheet and a water curable, isocyanate functional, prepolymer resin impregnated into the sheet; the ratio of isocyanate groups in the polyisocyanate to hydroxyl groups in the polyol being about 2:1 to about 3.5:1.

The subject matter of the present application is directed to an orthotic pad and method for forming an orthotic pad and utilizes some of the principles disclosed in the above-cited applications. For example, the orthotic pad of the present invention involves a resin-impregnated foam sheet as described in Ser. No. 15,972, although, by the use of modified resin systems, the instant pads remain generally less stiff and more resilient when cured. The orthotic pads of the present invention in fact utilize resin systems similar to those described in Ser. No. 903,281, in order to provide the desired combination of modulus and resilience. Other features and parameters have been discovered and carefully tailored such that a resin-impregnated foam sheet may be used effectively as an orthotic pad.

The word "modulus" as used herein refers to the force required to produce a unit of deformation, e.g., compression, in a cured resin-impregnated foam, i.e., modulus equals force/deformation. As such, it reflects the ability of the cured foam to comfortably support a body part, e.g., to provide proper weight-bearing strength for use in orthopedic applications. In turn, the "inverse of modulus" equals deformation/force. Thus, by using a constant force to compress different foams, one can measure and compare the percent deformation that each cured foam undergoes under that constant force.

The word "resilience", and inflected forms thereof, as used herein refers to the ability of a cured, resin-impregnated foam that has been compressed, to recover substantially its original dimensions within a given period of time. As such, it reflects the ability of the cured foam to provide a cushioning effect, i.e., to recover its cured shape within a period of time after compression, e.g., during use, such as walking in the case of an orthotic footpad. As will become apparent to those skilled in the art, modulus and resilience are dependent in part on such factors as the nature and/or density of the foam, the nature and/or amount of resin impregnated in the foam, the weight and/or cured density of the final unitary blank, and the extent of compression of the foam during curing, i.e., its initial density compared to its cured density.

Reference will now be made to the accompanying Drawing wherein like parts are designated with like numerals throughout.

Referring now to FIG. 1, there is shown in plan view a preferred blank 10 of the present invention dimensioned to be used in preparing an orthotic footpad. Blank 10 is generally comprised of a pliant, extensible foam sheet.

The foam sheet of blank 10 is open-celled, and a curable resin is impregnated in the foam sheet. As used herein, the term "open-celled" refers to a foraminous structure having interconnecting or communicating orifices or cavities therein caused by a sufficient number of the wall membranes of the foam cells having been removed. Further, as used herein, the word "impregnated" and inflected forms thereof refers to the condition in which the resin is intermingled with and in surrounding relation to the wall membranes of the cells and the interconnected cells of blank 10.

The foam sheet of blank 10 can comprise any one of a number of extensible foams that are open-celled, such as polyether- or polyester-based polyurethane foams. Importantly, the porosity of blank 10 must be such that it can be resin-loaded sufficiently to provide a satisfactory orthotic pad. In this regard, the open-celled foam sheet preferably has from about 10 to about 50 pores per centimeter (i.e., about 30 to about 120 pores per inch). As used herein, the term "pores per centimeter" refers to the average number of pores located along a linear centimeter of the foam sheet. The number of pores per linear centimeter may be determined in a number of ways known to those skilled in the art, for example, by photomicrographic means, or by measuring the foam's resistance to air flow or a pressure differential, and using such information to calculate the approximate number of pores in the foam.

When the number of pores per centimeter is decreased below about 10, the foams become too coarse or rough, and typically do not hold enough resin to either provide the necessary strength for the resulting orthotic pad or to retain the desired confirmation. Foam sheets having over about 50 pores per centimeter are not known to be presently commercially available. It will be understood, however, that the maximum number of pores per centimeter parameter is limited solely by the ability to load the foam with enough resin to provide sufficient properties for use as an orthotic pad. Since foam sheets having over 50 pores per centimeter are not presently available commercially, it is difficult to predict the performance of foams having substantially more than 50 pores per centimeter, e.g., as to their resin loading characteristics and porosity. Preferably, the open-celled foam sheet used to form blank 10 has from about 20 to about 40 pores per centimeter.

The dimensions of the foam sheet depends in large part on the intended use of the orthotic pad. An orthotic blank of the present invention can be prepared and packaged having dimensions intended for use in apposition to a particular type and/or size of body part. Generally, the most important dimension will be the thickness of the orthotic blank, i.e., the distance(s) between the major surface to be contacted with the body part, and the opposite surface thereto. The other dimensions of the foam sheet, e.g., those that determine the surface area of the body part to be supported and/or cushioned can be varied as desired, as will become apparent to those skilled in the art. Uncured blanks or cured pads can generally be trimmed, as with a blade or scissors, or by grinding or abrading, respectively, to provide a desired size and shape.

An orthotic blank intended for use as a pad within a shoe or boot for instance, e.g., as an innersole, will typically be of a thickness between about 0.5 cm and about 5 cm, and preferably between about 1 cm and about 3 cm. An orthotic blank intended for use as the sole of a sandal, on the other hand, could be of a thickness from on the order of a fraction of a centimeter to several, e.g., five or more centimeters. The foam sheet need not be of uniform thickness either, particularly in situations, for example, where a portion of a body part requires additional support or cushioning. For the orthotic footpad embodiment of FIGS. 1-5, a foam sheet approximately 10 cm wide, 30 cm long, and 2 cm thick is presently preferred.

Similarly, the resin-impregnated foam sheet can be used alone or in combination with other materials, e.g., to vary its thickness, to provide additional strength, to provide a custom wear surface, to more widely vary its density and so forth. Such other materials can include, for instance, resin-impregnated knit fabrics, or other resin-impregnated foam sheet materials, e.g., utilizing a different foam and/or resin in order to provide such different properties. These other materials could also include such materials as plastics, leather, metal and the like and may be applied before, during or after setting or curing of the impregnated foam. Preferably, such other materials are of a type that will bond themselves to the orthotic blank as it cures, by virtue of the inherent adhesive qualities of the resin used in the orthotic blank.

The foam sheet utilized in blank 10 preferably has a density in the range of about 0.02 to about 0.15 g/cm$^3$, and most preferably, between about 0.02 and about 0.07 g/cm$^3$. Foam sheets possessing densities lower than about 0.02 g/cm$^3$ are not known to be presently commercially available. Foam sheets having densities higher than about 0.15 g/cm$^3$ tend to preclude the ability to resin load the foam to the extent necessary to achieve proper strength.

Examples of suitable foam sheets include "E-100", "E-290", "P-60", "P-80" and "P-100", each available from Illbruck USA, Minneapolis, Minn. One presently preferred material for the foam sheet of the present invention is a polyether-based polyurethane foam sheet that is approximately 2 cm thick and is presently available from Illbruck USA, as type "E-150".

The most preferred resins for impregnating the foam sheet materials of the present invention are water-curable, isocyanate functional, polyurethane prepolymers prepared by the reaction of a polyol with an excess of a polyisocyanate. Suitable resins are disclosed, e.g., in copending U.S. application Ser. No. 903,281, and in U.S. Pat. No. 4,419,261, the disclosure of which is hereby incorporated by reference.

In order to obtain the desired modulus and resilience in a cured pad of the present invention, a significant factor in the choice of an appropriate polyol and an appropriate polyisocyanate to form the polyurethane prepolymer resin is the average hydroxyl equivalent weight, that is, the average molecular weight of the polyol(s) divided by the average number of reactive hydroxyl (OH) groups per mole of polyol(s). In general, the average hydroxyl equivalent weight of the polyol or polyol blend will be between about 400 grams and about 2400 grams, more preferably between about 1000 grams and about 2000 grams, and will preferably be greater than about 1000 grams when the isocyanate is polyaromatic, such as diphenylmethane diisocyanate.

Suitable polyols for use in the prepolymer resin include polyalkylene ethers derived from the condensation of alkylene oxides (such as those available from Union Carbide, South Charleston, W. Va., under the tradename "Niax" and from BASF Wyandotte Corp. under the tradename "Pluracol"), polytetramethylene ether glycols (such as the "Polymeg" polyols available from the Quaker Oats Co.), polycaprolactone polyols (such as the "Niax PCP" series of polyols available from Union Carbide), and polyester polyols (hydroxyl-terminated polyesters obtained from esterification of dicarboxylic acids and diols) such as the "Rucoflex" polyols available from Ruco division, Hooker Chemicals Co.

Examples of specific polyols that are useful include polypropylene glycols such as "PPG 2025" and "PPG 3025" available from Union Carbide, polypropylene triols such as "LHT 42" and "LHT 34", available from Union Carbide, and tetrols such as "Tetronic 1501" available from BASF Wyandotte Corp., Parsippany, N.J. Preferably all polyols used are urethane grade. The term "urethane grade" as used herein refers to polyols having a purity grade suitable for polyurethane production, as described, e.g., in Appendix B of *Polyurethanes—Chemistry and Technology*, J. H. Saunders and K. C. Frisch, eds., R. E. Krieger Publishing Co., Huntington, N. Y. (1978), the disclosure of which is hereby incorporated by reference.

However, it will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121-122 (1957) the disclosure of which is hereby incorporated by reference. Thus, for example, thiols and polyamines could also be used as "polyols" in the present invention and the term "polyols" will be considered to include such active hydrogen compounds. In such instances, the NCO:active hydrogen ratio of the polyisocyanate to the active hydrogen compound used to form the polythiocarbamate, polyurea, or other polymer, should fall within the same ranges as disclosed herein for the NCO:OH ratios.

Also in the present invention, the isocyanate equivalent weight of the prepolymer used is preferably relatively large. The isocyanate equivalent weight of the prepolymer is defined as the grams of prepolymer (i.e., polyol and isocyanate) per NCO group in the prepolymer. For purposes of the present invention, it has been found that the isocyanate equivalent weight should be within the range of about 400 grams to about 2300 grams of prepolymer per NCO group, and most preferably within the range of about 700 grams to about 1500 grams of prepolymer per NCO group.

Examples of isocyanates used to form polyisocyanates that are suitable for purposes of the present invention are disclosed, e.g., in U.S. Pat. Nos. 4,376,438, 4,433,680, and 4,502,479. Those isocyanates that are presently preferred include 2,4'-diphenylmethane diisocyanate, 4,4'-diphenylmethane diisocyanate, mixtures of these isomers together with possible small quantities of 2,2'-diphenylmethane diisocyanate (typical of commercially available diphenylmethane diisocyanates), and aromatic polyisocyanates and their mixtures, such as are derived from phosgenation of the condensation product of aniline and formaldehyde. It is presently preferred to use an isocyanate that has low volatility, such as diphenylmethane diisocyanate, rather than a more volatile material such as toluene diisocyanate. Commercially available isocyanate starting materials include "Isonate ® 143L" available from Dow Chemical, LaPorte, Tex., which is a mixture of isocyanate compounds containing about 73% by weight of diphenylmethane diisocyanate; "Mondur ® MRS-10" available from Mobay Chemical Corp., New Martinsville, W. Va.; and the polyaromatic polyisocyanate, "PAPI" available from Dow Chemical.

The NCO:OH ratio of the components of the prepolymer resin is preferably within the range of about 2:1 to about 8:1, and most preferably within the range of about 2.5:1 to about 4:1. It has been found that NCO:OH ratios lower than about 2:1 do not provide enough excess isocyanate groups to achieve adequate cross-linking of the resin during cure, while NCO:OH ratios greater than about 8:1 tend to produce undesirable stiffness. Higher NCO:OH ratios, i.e., approaching about 8:1, would generally be useful with polyols having higher hydroxyl equivalent weights.

Especially preferred resin components for use in the orthotic pads of the present invention are "Mondur ® MRS-10" isocyanate and "LHT-34" polyol available from Union Carbide. Another preferred resin may be formed by reacting the "Isonate ® 143L" isocyanate and the polypropylene oxide polyol available from Union Carbide as "LHT-42". To prolong the shelf life of orthotic blanks, it is preferred to include about 0.02 to about 0.1 percent (by weight based on the weight of the prepolymer resin) of benzoyl chloride and/or other suitable stabilizer (e.g., an antioxidant such as butylated hydroxy toluene at a level of about 0.05 to about 0.25 weight percent).

The term "resin system" as used herein refers to the prepolymer resin itself, i.e., the combination of polyol and isocyanate, as well as any other ingredients (e.g., catalyst(s), stabilizer(s), plasticizer(s), antioxidant(s), and the like) added to the prepolymer resin, or to either the polyol or isocyanate components thereof, prior to or simultaneously with their impregnation into the foam.

The resin systems of the present invention preferably contain a catalyst to control the set time and cure time of the resin. The term "set time" as used herein refers to the time needed for ar activated blank to hold its conformed shape. At this time it could be removed from contact with the body part while it continues to cure. The term "cure time" as used herein refers to the time needed for the resin therein to cross-link to the furthest extent it is going to cross-link under the conditions chosen.

During the set time the activated orthotic blank should exhibit an exotherm compatible for use in apposition to a mammalian body part, e.g., preferably an exotherm of less than about 43° C. and more preferably about 40° C. The resin system of the present invention, as will become apparent to those skilled in the art, can be adjusted in a variety of ways to obtain suitable exotherm during cure, e.g., by decreasing the resin-loading level; increasing the isocyanate equivalent weight of the prepolymer resin; reducing the NCO:OH ratio, and the like.

To produce suitable orthotic pads in accordance with the present invention, a set time of less than about 20 minutes following activation of the resin by exposure to water is preferred, with the most preferable set time being less than about 10 minutes. Frequently set times on the order of about 5 minutes or even about 4 minutes or about 3 minutes can be achieved. Suitable catalysts for moisture curing such prepolymer resins will become apparent to those skilled in the art. For example, tertiary amines such as 2,2'-dimorpholinodiethyl ether (DMDEE) described in U.S. Pat. No. 4,433,680, and 2,2'-dimorpholinyldialkyl ethers such as 4-[2-[1-methyl-2-(4-morpholinyl)-ethoxy]ethyl]morpholine (MEMPE) described in commonly assigned, copending application Serial No. 784,344, filed Oct. 4, 1985, in amounts ranging from about 0.5% to about 7% and preferably from about 2% to about 5% by weight, based on the weight of the prepolymer resin, may be used for this purpose.

Plasticizers can be, and preferably are, incorporated into the orthotic blank in order to maintain resilience of the cured orthotic pad over time, in a manner that will become apparent to those skilled in the art. For example, a plasticizer such as butyl benzylphthalate, available from Monsanto ("Santicizer 160") can be added to the resin system at between abort 1% and about 20% by weight, based on the weight of the prepolymer resin. A preferred amount of this plasticizer is between about 8% and about 12% by weight. The use of a plasticizer is particularly preferred in order to prepare resins having NCO:OH ratios approaching about 8:1, in that resins having such higher ratios (e.g., greater than about 4:1) tend to be stiff when used without plasticizer.

Preferably, and particularly when the orthotic pad is to be used in apposition to the skin itself, the resin system used therein is impregnated into the foam sheet in a solvent-less manner, i.e., without the use of solvents such as organic solvents, e.g., methylene chloride, and the like. Generally, resins having a viscosity of about 100,000 centipoise or less can be impregnated into the foam sheets without the use of solvents by methods that will become apparent to those skilled in the art, e.g., by manually squeezing or otherwise manipulating the resin system into the foam.

Resin systems having higher viscosities, e.g., greater than about 100,000 cps can generally also be impregnated into foam sheets without the use of solvents, e.g., in the manner described in copending U.S. Pat. application Ser. No. 15,972, wherein the polyol and isocyanate components of the prepolymer resin are blended immediately before impregnating into a foam sheet and allowed to react in situ in the foam sheet to form the prepolymer resin.

Preferably, the foam sheets of the present invention are impregnated with resin systems at coating weights of at least about 30% by weight of the total material, preferably at least about 40% by weight and particularly preferred are coating weights of at least about 50% by weight. Surprisingly, the prepolymer resin can often be impregnated into the foam sheets of the present invention so as to comprise as much as 80%, 90% and even 95% by weight while still retaining suitable moduli, resilience and conformability, depending on the foam and on the resin chosen.

The resin-impregnated foam sheets of the present invention are preferably prepared in a relatively low humidity chamber and sealed within a water vapor-impermeable package. This package is opened just prior to application of the blank.

Elements of the orthotic pads of the present invention and a presently preferred method by which orthotic pads can be formed in accordance with the present invention will now be described with reference to the Drawing.

Orthotic blank 10, as depicted in FIG. 1, is preferably used by: (1) "activating" the prepolymer resin, i.e., exposing the blank to water to initiate setting and curing of the resin; (2) if necessary, manually squeezing out excess water; (3) properly positioning the patient's foot on blank 10, if necessary with the use of an appropriate interface barrier; (4) keeping the foot in place as the resin sets, with sufficient pressure to cause the surface of the pad to become conformed to the shape of the bottom of the foot, and, if necessary; (5) trimming excess material from the cured orthotic pad in order to achieve the desired pad size or shape. The cured orthotic pad bears an impression of the foot, i.e., it conforms closely and permanently to the shape and position of those parts of the foot held in apposition to the blank during curing. The cured pad also provides proper weight-bearing strength and cushioning properties for its intended use, and, depending upon the varying degrees to which each portion of the blank was compressed during curing, the resultant orthotic pad exhibits variable modulus and resilience.

Figure 2:
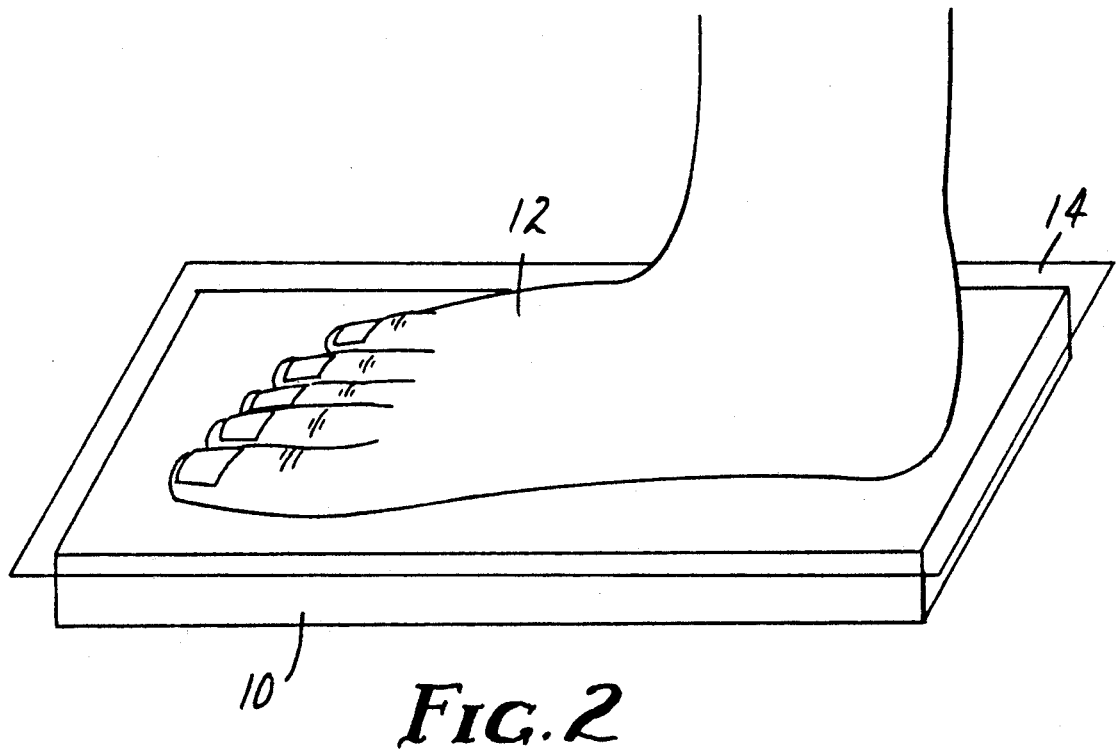
FIG. 2 is a perspective view of one side of the blank of FIG. 1 after it has been activated with water and while a foot is being positioned on it.

Before actually applying blank 10 to a body part, a flexible stockinet or other interface material 14, as depicted in FIG. 2, is preferably placed between the subject's skin and the orthotic blank so as to prevent undesirable adhesion or contact between blank 10 and the body part. For example, plastic sheet material such as Elastoflex TM "P" (available commercially from Clopay, Cincinnati, Ohio) having a thickness of about 0.038 mm (1.5 mil) can be placed over the blank prior to contacting it with the body part.

Figure 3:
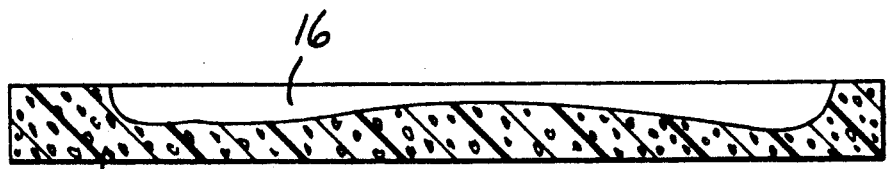
FIG. 3 is a longitudinal sectional view of the orthotic footpad of FIG. 2 after it has cured.
Figure 4:
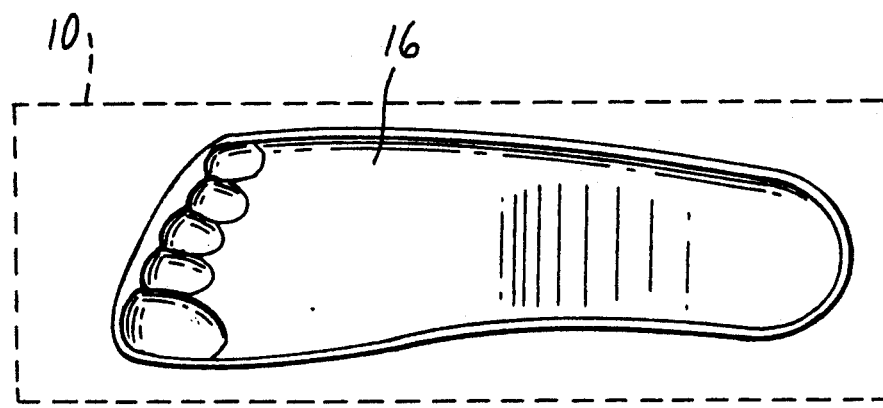
FIG. 4 is a plan view of the orthotic footpad after the excess material of blank 10 has been trimmed away.

An orthotic pad, as depicted in FIGS. 2, 3 and 4 is formed by first activating the resin of blank 10 of FIG. 1 with water. This can be accomplished, for example, by exposing it to water, e.g., dipping it in water, spraying it with water, and so on. Next, the blank 10 is preferably placed on or against a surface, e.g., a solid, flat surface, and longitudinally aligned with the patient's foot. In this regard, the resin-impregnated foam has excellent compression moldability and conformability to provide a good fit to the shape of the subject's foot.

Blank 10 is sufficiently dimensioned in its longest direction to extend at least the length of the foot to be supported and/or cushioned. Blank 10 is dimensioned in the other direction so as to extend at least the width of the foot. Clearly, blank 10 could be dimensioned to totally encompass or encompass only a portion of the foot, e.g., for use as a partial insert, or could be trimmed later to such dimensions.

With the subject's foot compressing blank 10 to the desired extent, blank 10 is maintained in apposition to the foot while the resin sets, optionally by the aid of means restraining or securing the foot in place.

Figure 5:
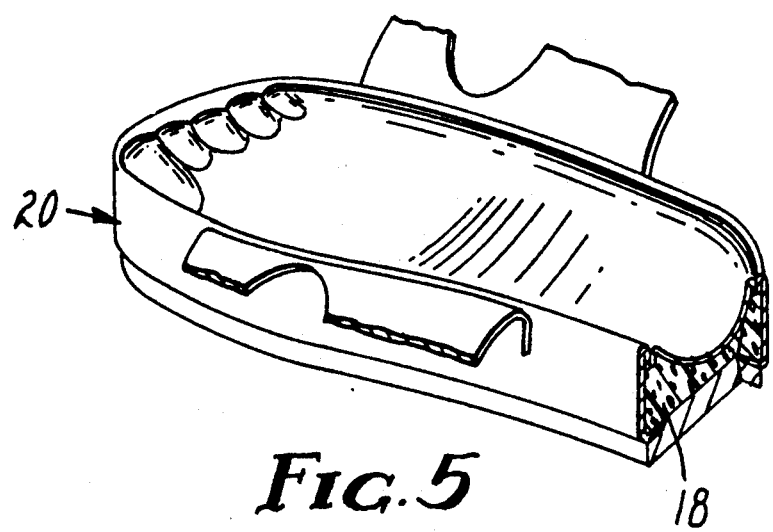
FIG. 5 is a perspective view of a sandal made from the orthotic footpad of FIG. 4, parts thereof broken away and shown in section.

After allowing sufficient time for curing, the resultant conformed and shaped orthotic pad bears an impression 16 of the foot and can be used in a variety of ways, e.g., as an insert in a shoe or boot, or as the sole of orthopedic footwear, e.g., as shown by its use as the sole 18 of the sandle 20 illustrated in FIG. 5.

It will be understood that various modifications and changes may be made by those skilled in the art to accommodate different situations.

The present invention will be further understood in view of the following examples which are merely illustrative and are not to be considered as comprehensive or limiting in any way.

EXAMPLE 1

In this example, an orthotic footpad within the scope of the present invention was prepared. First, a polyether-based polyurethane foam, having a thickness of approximately 1.95 cm was obtained from Illbruck USA (Minneapolis, Minn.) as type "E-100". This foam material has a density of about 0.02 g/cm$^3$ and a pore size of about 24 pores per linear centimeter. A 10.2 cm by 30.5 cm sheet of this foam material was cut out with a scissors. The weight of the foam sheet was determined to be about 12 grams, and this figure was used to determine the correct amount, in grams, of the resin system to be used in order to achieve a resin loading of about 85% by weight of the final resin-impregnated foam sheet.

A polyurethane prepolymer resin having an NCO:OH ratio of about 3.0:1 was prepared as follows. In an atmosphere maintained at about 4% relative humidity, a vessel was charged with 396 grams of isocyanate ("Mondur ® MRS-10," obtained from Mobay Chemical). (This isocyanate compound has an NCO equivalent weight of about 132 grams of isocyanate per NCO group.) A second vessel was charged with 1650 grams of "LHT-34" as the polyol, which was obtained from Union Carbide. (The LHT-34 had an OH equivalent weight of about 1650 grams of polyol per OH group.) To the LHT-34 in the second vessel was added 0.4 grams of benzoyl chloride as stabilizer, 236 grams of butyl benzylphthalate ("BBPTH", Monsanto) as plasticizer, and 85 grams of 4-[2-[1-methyl-2-(4-morpholinyl)-ethoxy]ethyl]morpholine ("MEMPE") as catalyst, prepared as described in Example 1 of copending application Ser. No. 784,344, filed Oct. 4, 1985, the disclosure of which is hereby incorporated by reference. The mixture in the second vessel was then added to the isocyanate compound contained in the first vessel, and the components were blended together. (This prepolymer mixture had an NCO equivalent weight of about 1023 grams of prepolymer resin per NCO group.) Immediately after blending these components together, the blender resin system was impregnated into the foam sheet in an amount such that the resin system represented about 85% by weight of the final product. Such impregnation of the resin system into the foam sheet was achieved in a moisture-free chamber by spreading the resin system over all surfaces of the foam sheet and then manually kneading the resin system into the foam material. The viscosity of the resin system 24 hours after blending the components (to allow sufficient time for reaction to occur) was determined to be about 20,000 centipoise, using a Brookfield viscometer, Model RV, Brookfield Engineering Laboratories, Stoughton, Mass. The blank thus prepared was then sealed in an air-tight pouch to protect the blank from exposure to moisture.

Later, the blank prepared in this Example 1 was applied to a foot by the following procedure. The impregnated foam blank was removed from the pouch, and activated by dipping in room temperature water. Excess water was removed by squeezing. The activated, impregnated foam blank was covered with a 0.038 mm (1.5 mil) thick film of Elastoflex "P", available from Clopay Co. A subject's bare foot was then settled into the foam blank causing the foam to conform in shape to the heel, sole and lower sides of the foot. Care was taken not to completely compress the foam under the heel or ball of the subject's foot.

After being held in place for about five minutes, the foot was removed from the foam blank leaving an exact impression of the subject's foot. The Elastoflex "P" film was peeled off and when cured, the orthotic pad was trimmed as necessary with a scissors and hand held grinder (Dremel "Moto Tool", Sears Roebuck) to fit the subject's shoe as an insert. The finished insert conformed exactly to the subject's foot, provided excellent support and cushioning, particularly in the arch area, and was comfortable to wear.

EXAMPLE 2

In this example, an orthotic shinpad within the scope of the present invention was prepared according to the procedure of Example 1 with the following exceptions. In this Example 2, a polyurethane prepolymer resin having an NCO:OH ratio of about 2.5:1 was prepared by charging the first vessel with 360 grams of isocyanate ("Isonate® 143L", obtained from Upjohn and having an NCO equivalent weight of about 144 grams of isocyanate per NCO group). The second vessel was charged with 1335 grams of polyol ("LHT-42", obtained from Union Carbide), and 0.17 grams of benzoyl chloride as stabilizer, 188 grams of BBPTH as plasticizer, and 67 grams of MEMPE as catalyst. In this example, the resin system, i.e., the prepolymer resin itself as well as the stabilizer, plasticizer and catalyst represented about 80% by weight of the final product, and the prepolymer resin had an NCO equivalent weight of about 1130 grams of prepolymer resin per NCO group. The blended resin system had a measured viscosity of approximately 22,000 centipoise. A stockinette was placed over a subject's lower leg. The water activated, impregnated foam blank was positioned against the stockinette and over the shin area. Using a stretch bandage overwrap, the impregnated foam blank was partially compressed and conformed to the shin as it cured. The temperature that would be felt by the patient during curing was determined to be less than about 39° C., using a thermometer placed under the blank as it cured. The orthotic shinpad formed in this example was sufficiently set after about 5 minutes from the initial activation of the prepolymer resin. The cured shinpad was trimmed to remove any excess material. The finished pad was soft and resilient and retained the exact shape of the subject's shin. When held in place with an elastic bandage or stockinette the pad offered excellent protection for the shin.

EXAMPLES 3–14

The inverse modulus and resilience of a variety of pads of the present invention were compared by the following means, using force and time values that roughly approximate the forces and times an orthotic footpad would be expected to be subjected to in the course of a subject walking.

The inverse modulus values given below represent the observed percent (%) deformation of each cured pad in response to a load of 1.05 kg/cm$^2$ (15 psi) applied over a period of 0.5 seconds.

Resilience was calculated as the percent of its original dimensions a cured pad recovers within 0.5 seconds, after being deformed (compressed) to one-half of its cured thickness.

Both inverse modulus and resilience were calculated for orthotic pads cured at both 0 and 50% compression, i.e., cured at both their original, uncompressed, thickness, and cured at a 50% compressed thickness.

The experimental method used to calculate modulus and resilience was as follows:

Cyclic stress-strain experiments were performed using an MTS 810 Material Test System (MTS Systems Corp., Minneapolis, Minn.). All experiments were performed at a frequency of 1 Hertz in a haversine displacement mode as controlled by the 410 Digital Function Generator. The 442 Controller was adjusted so that actuator displacement and load cell output corresponded to 1.27 cm/volt (0.5 inch/volt) and 13.6 kg/volt (30 pounds-force/volt), respectively. All loads were measured using an MTS Model 661.21A-01 Load Cell. Actuator linear variable displacement transducer "LVDT" and load cell voltages were recorded by a Nicolet 4094 Digital Oscilloscope. (Nicolet Instruments, Madison, Wisc.)

A 10.16 cm (4 inch) diameter, 2.54 cm (1 inch) thick steel disc test fixture was attached to the MTS load cell. A 15.24 cm (6 inch) diameter, 2.54 cm (1 inch) thick steel disc test fixture was attached to the MTS actuator. As employed for testing, the load cell and actuator discs were coaxially aligned and the faces of each disc were parallel to each other. The test specimen was sandwiched between these two discs as tested. Movement of the actuator disc toward the load cell disc would result in sample compression and produce a force on the load cell disc.

Tested samples measured approximately 12.7 cm × 15.24 cm (5 inch × 6 inch). In all cases samples were sufficiently wide enough to completely cover the face of the load cell disc. The tested samples were 1.65 to 2.16 cm (0.65 to 0.85 inch) thick for the uncompressed-cured samples and 0.83 to 1.08 cm for the 50% compressed-cured samples.

To obtain the inverse modulus (% deformation) values, the MTS system was used in the load control mode where a continuous sinusoidal loading was maintained on the load cell and the necessary actuator displacement needed to maintain the programmed load was monitored. The sample to be measured was first placed between the test fixture discs and the actuator was positioned so that the preload force on the sample was 16.8 g/cm$^2$ (0.24 psi) (corresponding to a load cell voltage output of 0.10 volt). The 442 Controller was adjusted so that this position corresponded to an actuator LVDT output of zero volts. During the experiment, the actuator position was adjusted by the 442 Controller so that the force on the load cell varied sinusoidally between 1.36 and 85.7 kg (3.0 and 188.5 pounds-force) corresponding to a sample loading of 0.0168 and 1.055 kg/cm$^2$ (0.24 15.0 psi), respectively. The voltages corresponding to the position of the actuator and the force on the load cell were monitored by the Nicolet 4094 Digital Oscilloscope. The stress-strain hysteresis loop was monitored until no changes due to sample relaxation were observed. Four consecutive hysteresis loops were then stored in the oscilloscope pending analysis.

To obtain the resilience (% recovery) values, the MTS system was used in the stroke control mode where a continuous sinusoidal displacement of fixed amplitude was applied to the actuator and the resulting force on the load cell was monitored. The sample to be measured was first placed between the test fixture discs and the actuator disc was positioned so that the preload force on the sample was 16.8 g/cm$^2$ (0.24 psi) (corresponding to a load cell voltage output of 0.10 volt). The 442 Controller was adjusted so that this position corresponded to an actuator LVDT output of zero volts. The distance between the disc faces was measured and the 442 Controller was adjusted so that the maximum displacement of the actuator during the test would be exactly one-half of the disc face distance. During the experiment, the actuator cycled sinusoidally between its zero position and a point at which the disc face separation was 50% of the initial separation. The voltages corresponding to the position of the actuator and the force on the load cell were monitored by the Nicolet 4094 Digital Oscilloscope. The stress-strain hysteresis loop was monitored until no changes due to sample relaxation were observed. Four consecutive hysteresis loops were then stored in the oscilloscope pending analysis.

A variety of orthotic pads were prepared and their inverse moduli and resilience calculated according to the above procedures, the results of which are listed below in TABLE I.

Resins were prepared as described in Example 2, using Isonate ® 143L as the isocyanate, and a final concentration in the resin system of 0.07% benzoyl chloride (as stabilizer), 4.0% MEMPE (as catalyst) and 0.2% butylated hydroxytoluene (as stabilizer). None of the samples contained plasticizer. As the polyol, Examples 3–8 were prepared in pairs using triols of varying OH equivalent weights (1650, 2000 and 1350, respectively) and Examples 9–14 were prepared in pairs using diols of varying OH equivalent weights (1500, 500 and 1000, respectively). The odd-numbered Examples of each pair were prepared at an NCO:OH ratio of 2.5:1, and the even numbered at 3:1.

The orthotic pads were each prepared using 1.9 cm (¾ inch) thick foam ("E-150") impregnated at an 85% resin system coating weight. The OH equivalent weight of the polyols used was varied as shown in TABLE I. Also listed in TABLE I are the subjective determination ("comments") of the suitability of each pad for use as an orthotic pad.

TABLE I

| Ex. | polyol (OH eq. wt) | Inverse Modulus (% deformation) | | Resilience (% recovery) | | Comments |
|---|---|---|---|---|---|---|
| | | Un-comp. | 50% Comp. | Un-comp. | 50% Comp. | |
| 3 | 1650 triols | 80 | 53 | 45 | 87 | Excellent |
| 4 | 1650 triols | 76 | 42 | 51 | 91 | " |
| 5 | 2000 triols | 80 | 57 | 40 | 82 | " |
| 6 | 2000 triols | 78 | 47 | 46 | 90 | " |
| 7 | 1350 triols | 77 | 42 | 51 | 92 | " |
| 8 | 1350 triols | 78 | 44 | 49 | 91 | " |
| 9 | 1500 diols | 80 | 47 | 30 | 81 | Useful |
| 10 | 1500 diols | 80 | 50 | 35 | 78 | " |
| 11 | 500 diols | 77 | 38 | 32 | 71 | Stiff |
| 12 | 500 diols | 63 | 23 | 40 | 73 | " |
| 13 | 1000 diols | 78 | 45 | 39 | 86 | Useful |
| 14 | 1000 diols | 79 | 47 | 38 | 81 | " |

As seen in TABLE I, preferable orthotic pads prepared as described in Examples 3–14 exhibit inverse moduli (in the uncompressed and 50% compressed states) of between about 40% and about 100% deformation, and preferably between about 45% and about 90% deformation, in response to a load of 1.05 kg/cm$^2$ applied over a period of 0.5 seconds. Correspondingly, preferable orthotic pads prepared as described in these Examples exhibit resilience (in the uncompressed and 50% compressed states) of between about 30% and about 100% recovery, and preferably between about 40% and about 100% recovery, within 0.5 seconds, after being deformed to one-half their cured thickness. Generally, suitable orthotic pads of the present invention will recover essentially all of their original shape within a reasonable period of time for use, e.g., within seconds of their being deformed.

We claim:

1. A method of supporting and/or cushioning a mammalian body part by the use of an orthotic pad, which method comprises the step of using as said orthotic pad an open-celled foam conformed to the shape and position of said body part by the use of a cured polyurethane resin impregnated therein, wherein said pad is prepared from an orthotic blank that when cured in the uncompressed state or the 50% compressed state would exhibit, in both status, an inverse modulus of greater than about 40% deformation in response to a load of 1.05 Kg/cm$^2$ over a period of 0.5 second, and a resilience of greater than about 30% recovery within 0.5 seconds after being deformed to one-half its cured thickness.

2. An orthotic blank comprising an open-celled foam having dimensions suitable for use in apposition to a body part and impregnated with a resin system, said resin system comprising
   a. a water curable prepolymer resin comprising an isocyanate component and a polyol component, said polyol component having an average hydroxyl equivalent weight greater than about 400 grams of polyol per hydroxyl group, and
   b. a catalyst capable of setting and curing said prepolymer resin upon exposure to water, wherein said orthotic blank, when cured in the compressed state, or the 50% compressed state would exhibit, in both states, an inverse modulus of greater than about 40% deformation in response to a load of 1.05 kg/cm$^2$ over a period of 0.5 seconds, and a resilience of greater than about 30% recovery within 0.5 seconds after being deformed to one-half its cured thickness.

3. An orthotic blank according to claim 2 wherein said resin system is impregnated into said foam without the use of solvents.

4. An orthotic blank according to claim 2 wherein said blank sets within about 10 minutes after the activation of said catalyst by exposure to water.

5. An orthotic blank according to claim 2, wherein said blank, after activation and while setting, exhibits an exotherm of about 43° C. or less.

6. An orthotic blank according to claim 2 wherein said polyol component is a polypropylene triol.

7. An orthotic blank according to claim 2 wherein said resin system further comprises plasticizer.

8. An orthotic blank according to claim 2 wherein said catalyst is 2,2'-dimorpholinodiethyl ether, present in an amount of from about 0.5% to about 7% by weight based on the weight of the prepolymer resin.

9. An orthotic blank according to claim 2 wherein said catalyst is 4-[2-[1-methyl-2-(4-morpholinyl)ethoxy]ethyl]morpholine, present in an amount of from about 0.5% to about 7% by weight based on the weight of the prepolymer resin.

10. An orthotic blank according to claim 2 wherein said foam has dimensions suitable for the preparation of an orthotic footpad.

11. An orthotic blank according to claim 2 wherein said blank is used in conjunction with an orthopedic brace.

12. An orthotic pad bearing the impression of a body part and prepared from an orthotic blank, comprising an open-celled foam impregnated with a resin system, said resin system comprising
   a. a water curable prepolymer resin comprising an isocyanate component and a polyol component, said polyol component having an average hydroxyl equivalent weight greater than about 400 grams of polyol per hydroxyl group, and
   b. a catalyst capable of setting and curing said prepolymer resin upon exposure to water
wherein said blank, when cured in the uncompressed state or the 50% compressed state would exhibit, in both states, an inverse modulus of greater than about 40% deformation in response to a load of 1.05 kg/cm$^2$ over a period of 0.5 seconds, and a resilience of greater than about 30% recovery within 0.5 seconds after being deformed to one-half its cured thickness.

13. An orthotic pad according to claim 12 wherein said blank sets within about 10 minutes after the activation of said prepolymer resin by exposure to water.

14. An orthotic pad according to claim 13 wherein said catalyst is 2,2'-dimorpholinodiethyl ether, present in an amount of from about 0.5% to about 7% by weight based on the weight of the prepolymer resin.

15. An orthotic pad according to claim 13 wherein said catalyst is 4-[2-[1-methyl-2-(4-morpholinyl)ethoxy]ethyl]morpholine, present in an amount of from about 0.5% to about 7% by weight based on the weight of the prepolymer resin.

16. An orthotic pad according to claim 12 wherein said foam is a polyether-based polyurethane foam.

17. An orthotic pad according to claim 12 wherein said foam is a polyester-based polyurethane foam.

18. An orthotic pad according to claim 12 wherein said pad is an orthotic footpad.

19. An orthotic footpad according to claim 18 wherein said footpad exhibits variable modulus and resilience.

20. An orthotic pad according to claim 12 wherein said pad is used in conjunction with an orthopedic brace.

21. A sandal comprising a sole which comprises an orthotic footpad bearing the impression of a foot and prepared from an orthotic blank comprising an open-celled foam impregnated with a resin system, said resin system comprising
   a. a water curable prepolymer resin comprising an isocyanate component and a polyol component, said polyol component having an average hydroxyl equivalent weight greater than about 400 grams of polyol per hydroxyl group, and
   b. a catalyst capable of setting and curing said prepolymer resin upon exposure to water wherein said blank, when cured in the uncompressed state or the 50% compressed state would exhibit, in both states, an inverse modulus of greater than about 40% deformation in response to a load of 1.05 kg/cm$^2$ over a period of 0.5 second, and a resilience of greater than about 30% recovery within 0.5 seconds after being deformed to one-half its cured thickness.

22. An orthotic pad prepared from an orthotic blank and substantially conformed to the shape and position of a body part, wherein said blank, when cured in the uncompressed state of the 50% compressed state would exhibit, in both states, an inverse modulus of greater than about 40% deformation in response to a load of 1.05 kg/cm$^2$ over a period of 0.5 seconds, and a resilience of greater than about 30% recovery within 0.5 seconds after being deformed to one-half its cured thickness.

* * * * *